(12) United States Patent
Batesole (10) Patent No.: US 8,805,048 B2
(45) Date of Patent: Aug. 12, 2014

(54) METHOD AND SYSTEM FOR ORTHODONTIC DIAGNOSIS

(76) Inventor: Mark Batesole, Laguna Niguel, CA (US)

(*) Notice: Subject to any disclaimer, the term of this patent is extended or adjusted under 35 U.S.C. 154(b) by 415 days.

(21) Appl. No.: 13/071,231

(22) Filed: Mar. 24, 2011

(65) Prior Publication Data
US 2011/0244415 A1    Oct. 6, 2011

Related U.S. Application Data

(60) Provisional application No. 61/320,171, filed on Apr. 1, 2010.

(51) Int. Cl.
*G06K 9/00* (2006.01)

(52) U.S. Cl.
USPC ............. 382/132; 600/416; 600/587; 433/24; 345/634

(58) Field of Classification Search
USPC ..................... 382/132; 600/416, 587; 433/24; 345/634
See application file for complete search history.

(56) References Cited

U.S. PATENT DOCUMENTS

| | | | |
|---|---|---|---|
| 5,278,756 A * | 1/1994 | Lemchen et al. ............. | 600/587 |
| 5,318,441 A | 6/1994 | Keller | |
| 5,659,625 A * | 8/1997 | Marquardt .................... | 382/118 |
| 5,802,133 A * | 9/1998 | Kawai et al. ........................ | 378/4 |
| 5,867,588 A * | 2/1999 | Marquardt .................... | 382/118 |
| 5,951,498 A | 9/1999 | Arnett | |
| 6,464,496 B1 | 10/2002 | Sachdeva et al. | |
| 6,648,640 B2 | 11/2003 | Rubbert et al. | |
| 6,711,297 B1 | 3/2004 | Chang et al. | |
| 6,725,231 B2 | 4/2004 | Hu et al. | |
| 6,888,546 B1 * | 5/2005 | Kim .............................. | 345/424 |
| 6,909,795 B2 | 6/2005 | Tecotzky et al. | |
| 6,912,319 B1 | 6/2005 | Barnes et al. | |
| 7,006,099 B2 | 2/2006 | Gut et al. | |

(Continued)

FOREIGN PATENT DOCUMENTS

EP    0534548 B1    1/1998

OTHER PUBLICATIONS de Oliveira et al., "Observer reliability of three-dimensional cephalometric landmark identification on cone-beam computerized tomography", Feb. 2009, Oral Surgery, Oral Medicine, Oral Pathology, Oral Radiology, and Endodontology, vol. 107, Issue 2, 256-265.*

(Continued)

*Primary Examiner* — Jason M Repko
*Assistant Examiner* — Katrina Fujita
(74) *Attorney, Agent, or Firm* — Stetina Brunda Garred & Brucker (57) ABSTRACT

A method for generating a cephalometric analysis of an orthodontic patient is disclosed. A sequence of images that may each correspond to a specific anatomical plane of the patient is received. Then, a volumetric representation of the patient is derived from a combination of the sequence of the images. One or more markers associated with particular anatomical landmarks of the patient according to a predefined analysis method are received. The markers are defined by a set of coordinate values, and are designated via an interactive user interface to a two-dimensional representation derived from the volumetric representation. Connectors between one or more of the markers are generated in accordance with the predefined analysis method, and a visual representation of the markers and the connectors are overlaid on the volumetric representation.

16 Claims, 9 Drawing Sheets

(56) References Cited

U.S. PATENT DOCUMENTS

| | | |
|---|---|---|
| 7,361,018 B2 | 4/2008 | Imgrund et al. |
| 7,526,132 B2 | 4/2009 | Koenig |
| 7,613,335 B2 * | 11/2009 | McLennan et al. ........... 382/128 |
| 2003/0101079 A1 | 5/2003 | McLaughlin |
| 2007/0003900 A1 | 1/2007 | Miller |
| 2007/0197902 A1 * | 8/2007 | Schutyser .................... 600/416 |
| 2008/0096151 A1 | 4/2008 | Cinader, Jr. et al. |
| 2009/0003667 A1 | 1/2009 | Cheng et al. |

OTHER PUBLICATIONS

Mohseni et al., "Automatic Localization of Cephalometric Landmarks", 2007 IEEE International Symposium on Signal Processing and Information Technology, 396-401.* http://dicom.nema.org.

* cited by examiner

METHOD AND SYSTEM FOR ORTHODONTIC DIAGNOSIS

CROSS-REFERENCE TO RELATED APPLICATIONS

This application claims the benefit of U.S. Provisional Application No. 61/320,171, filed Apr. 1, 2010.

STATEMENT RE: FEDERALLY SPONSORED RESEARCH/DEVELOPMENT

Not Applicable

BACKGROUND

1. Technical Field

The present disclosure relates generally to the field of orthodontics. More particularly, the present disclosure relates to a method and system for diagnosing, planning and presenting an orthodontics treatment.

2. Related Art

The specialized practice of orthodontics involves the study and treatment of malocclusions, or misalignment of teeth, for improved function and appearance. In general, treatment involves the use of various active, passive and functional orthodontic appliances to correct and secure alignment of the teeth. Common active appliances include brackets that are bonded to the patient's teeth and coupled together with an arched wire. The wire exerts a force on the bracket, which in turn exerts a force on the teeth, thereby causing the teeth to move. More particularly, stresses created within the periodontal ligament by the archwire results in bone remodeling, where bone is created on one side and resorbed on the other side. Once the teeth have moved to the desired location and held in place for a period of time, bone and tissue undergo development that maintains the positioning. To further aid in maintaining the position of the teeth, the patient may wear passive devices such as retainers, which typically consist of a metal wire that surrounds the teeth.

In prescribing an orthodontic treatment, the practitioner evaluates a wide range of data. These include the patient's medical, dental, and orthodontic histories, as well as various images of the patient's teeth, jaws, and head structures. These images are conventionally obtained as radiographs (X-ray images), photographs, and increasingly, computer tomography (CT) scans. Physical, three-dimensional models using plaster of Paris may be constructed from impressions taken of the patient's upper and lower jaws. The foregoing information is used to recognize the various characteristics of malocclusion, and to develop a specific treatment strategy that details each desired movement of the orthodontic structures that may be based upon a post-treatment model. The practitioner constantly evaluates updated data as treatment progresses in order to make adjustments to the orthodontic appliances.

One commonly used diagnostic is the cephalometric analysis, where relationships of dental and skeletal structures are evaluated. X-ray images of the patient's head are taken, and anatomical landmarks are plotted on the images. The typical views utilized are the posterior-anterior view and the lateral view. Connectors are then plotted between various landmarks. Based upon the length and angular relationships to other connectors, various orthodontic characteristics are quantified. These measurements may then be compared to statistical norms for a given age and ethnic background to determine a treatment plan that corrects the anomalous features. The measurements are helpful in comparing dental relations as well as skeletal relations, and the determination of soft tissue outlines.

The earliest techniques involved the manual plotting of the landmarks and connectors on the X-ray acetate sheets. That proved to be a tedious and time-consuming process. Accuracy and repeatability was also problematic. Conventionally, the two-dimensional X-ray images may be digitized, and the plotting performed by computer input. However, the process remained tethered to the two dimensional sphere, and was inadequate for an inherently three-dimensional environment.

As noted, it is necessary for the practitioner to evaluate updated patient information as treatment adjustments are made. With respect to cephalometric analysis, updated radiograms are essential, and the initial cephalogram alone is insufficient. One difficulty associated with earlier radiograms is the deviations of the positioning of the head from one image to another. Thus, tracking the patient's progress based on comparisons of the different cephalograms proved to be difficult. In response to this problem, devices known in the art as cephalostats have been developed, which holds the head stationary at a specific distance and orientation. Instead of simple X-ray devices, computer tomography (CT) imaging modalities such as cone beam computed tomography (CBCT) are increasingly favored. These modalities are capable of generating three-dimensional images, but typically lack cephalostats.

Accordingly, there is a need in the art for an improved method and system for orthodontic diagnosis.

BRIEF SUMMARY

In accordance with one embodiment of the present disclosure, a method for generating a cephalometric analysis of an orthodontic patient is contemplated. The method includes receiving a sequence of images that may each correspond to a specific anatomical plane of the orthodontic patient. Thereafter, a volumetric representation of the orthodontic patient may be derived from a combination of the sequence of the images. One or more markers are then received. The markers may be associated with particular anatomical landmarks of the orthodontic patient according to a predefined analysis method. The markers may be defined by a set of coordinate values and designated via an interactive user interface to a two-dimensional representation derived from the volumetric representation. The method may also include generating connectors between one or more selected markers in accordance with the predefined analysis method. Thereafter, the method may continue with overlaying a visual representation of the markers and the connectors on the volumetric representation.

Another embodiment contemplates a method for developing an orthodontic treatment plan. The method may include receiving a first sequence of images of an orthodontic patient. Additionally, the method may include generating a first cephalogram from the first sequence of images and a plurality of landmarks of orthodontic structures identified on the images. The first cephalogram may include properties specifying particular relationships between one or more of the plurality of landmarks in accordance with an analysis method. A volumetric representation of the orthodontic patient may be displayed, which may be based upon the sequence of images with the first cephalogram being overlaid thereon. The method may also include receiving adjustments to one or more of the properties, and generating a second cephalogram from the adjusted properties.

The present invention will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which.

Common reference numerals are used throughout the drawings and the detailed description to indicate the same elements.

DETAILED DESCRIPTION

The detailed description set forth below in connection with the appended drawings is intended as a description of certain embodiments of the present disclosure, and is not intended to represent the only forms that may be developed or utilized. The description sets forth the various functions in connection with the illustrated embodiments, but it is to be understood, however, that the same or equivalent functions may be accomplished by different embodiments that are also intended to be encompassed within the scope of the present disclosure. It is further understood that the use of relational terms such as top and bottom, first and second, and the like are used solely to distinguish one entity from another without necessarily requiring or implying any actual such relationship or order between such entities.

An application for aiding in the diagnosis, treatment planning and presentation of an orthodontic case by visualizing a patient's anatomical features is contemplated. The application implements a method for generating a cephalometric analysis of an orthodontic patient as one or more computer-executable instructions stored on a storage medium. Furthermore, the application also implements a method for developing an orthodontic treatment plan.

In accordance with one embodiment, the application is a set of software instructions executed on a conventional personal computer platform having data processing and storage capabilities, as well as a graphical user interface. Although the various methods introduced in the present disclosure are described in relation to a software application, it will be appreciated that the methods are not limited thereto. Conventional computer platforms include those that utilize the MacOS operating system or the Windows operating system, among several others.

As indicated above, the application visualizes the patient's anatomical features on the computer, that is, displays images representative of the patient as obtained from various medical imaging modalities on an output device. With reference to the flowchart of FIG. 1, the method for generating a cephalometric analysis begins with a step 300 of receiving a sequence of images each corresponding to a specific anatomical plane of the head of the patient. One contemplated imaging modality is cone beam computed tomography (CBCT), though any other modality, whether currently known or unknown, may be readily substituted. As is well understood in the art, CBCT and other tomography modalities generate successive sectional images of a three-dimensional object taken along a single axis or rotation. A three-dimensional or volumetric representation of the orthodontic patient may then be derived from a combination of the sequence of images according to step 302. It is to be understood that while the contemplated methods set forth in the present disclosure are described in terms of one step occurring before or after another, it is by way of example only and not of limitation, and the methods may proceed in accordance with any order.

Figure 2:
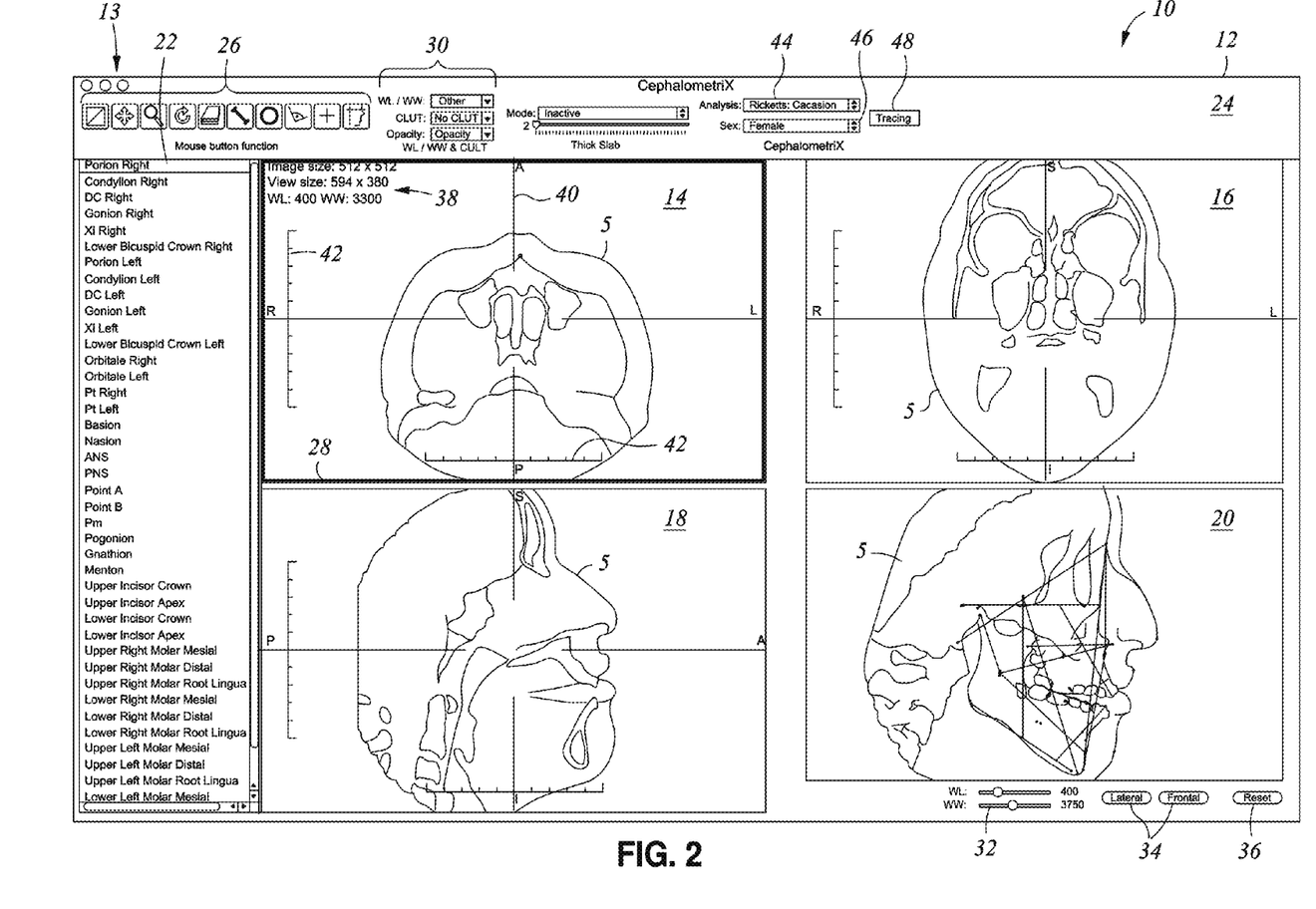
FIG. 2 is an exemplary marker placement user interface of a plug-in module for an image viewer application that embodies the method for generating the cephalometric analysis.

Medical imaging modalities typically generate outputs in the DICOM, or Digital Imaging and Communications in Medicine format, and in accordance with one embodiment, the contemplated method for generating a cephalometric analysis may be implemented as a plug-in module to a general-purpose image viewer application capable of displaying DICOM image data. One such image viewer application is the open source application OsiriX, which runs on the MacOS platform. FIG. 2 shows one exemplary user interface 10 of the plug-in module, which is understood to be an extension of the underlying image viewer application. Accordingly, various user interface components are inherited therefrom. It is to be understood, however, that the disclosed methods are not limited to implementation on such an application architecture, and may be implemented on other medical imaging applications or developed as a standalone application.

Generally, the user interface 10 includes a placement window 12 segregated into various viewing panes 14, 16, 18, and 20, as well as a landmark selection pane 22, the details of which will be discussed more fully below. The placement window 12 has a set of window control buttons 13 that provides various windowing manipulations including the well known maximize, minimize, and close functions. The viewing panes present various views of the sequence of images received in step 300 and stored in the DICOM data. As indicated above, the images are sectional views of the patient's head 5. These include an axial view shown in the first viewing pane 14, a coronal view shown in the second viewing pane 16, a saggital view shown in the third viewing pane 18, and a volumetric maximum intensity projection (MIP) view shown in the fourth viewing pane 20.

It is understood that each of the viewing panes are independently navigable, that is, zoom levels, view positioning, segment selection, and so forth can be individually manipulated from one viewing pane to another. The placement window 12 also includes a toolbar 24 with one or more navigation icons 26 that can be selected to invoke these functions. For example, selecting the multi-directional arrow and dragging the cursor in different directions may result in the view being shifted accordingly. Some navigation functions may be performed independently of other panes, but functions such as zoom level changes may involve coordinating between the panes. Those having ordinary skill in the art will be able to determine which functions are better synchronized, depending on the circumstances. Prior to navigating within any of the viewing panes 14-20, the desired viewing pane is selected. A selected viewing pane is delineated in part by a thickened outer border 28. According to one embodiment, the navigation icons 26 and the functions and adjustments provided thereby are understood to be defined in the DICOM image viewer application.

The toolbar 24 also includes display parameter controls 30 that variously adjust the way the images are outputted. For instance, image contrast can be adjusted by setting the window level (WL) and window width (WW) parameters. Different coloring effects may be set by a selection of a Color Look-Up Table (CLUT), and the opacity of the structures may also be changed. Like the navigation icons 26, the display parameter controls 30 and the adjustments are understood to be defined in the underlying image viewer application.

Referring specifically to the fourth viewing pane 20 with the volumetric MIP view, the WL and WW parameters may be separately adjusted via sliders 32. Furthermore, as the volumetric representation is three-dimensional, separate navigation controls that rotate the patient's head 5 along the x and y axes are available. A default view position, either a lateral or frontal view may be selected by view selection buttons 34. The view position may also be reset via a reset button 36.

The present disclosure refers to various graphical user interface navigation functions that typically involve the movement of a mouse, and the pressing of buttons thereon to invoke additional functionality. Alternative input devices are understood to have similar, corresponding input actions that invoke the same functionality, and are deemed to be equivalents. Thus, the specific graphical user interface navigation functions referenced herein are presented by way of example only and not of limitation.

At the corner of the first viewing pane 14, there is an image information overlay 38 that describes the various properties of the sequence of images including the image size, viewing size, and contrast settings (window length, window width). According to one embodiment, the image information overlay 38 is displayed on the selected viewing pane. Furthermore, crosshairs 40 and vertical and horizontal scales 42 are also overlaid on each of the viewing panes 14-20 to designate the center and dimensions, respectively, of the patient's head 5.

Figure 1:
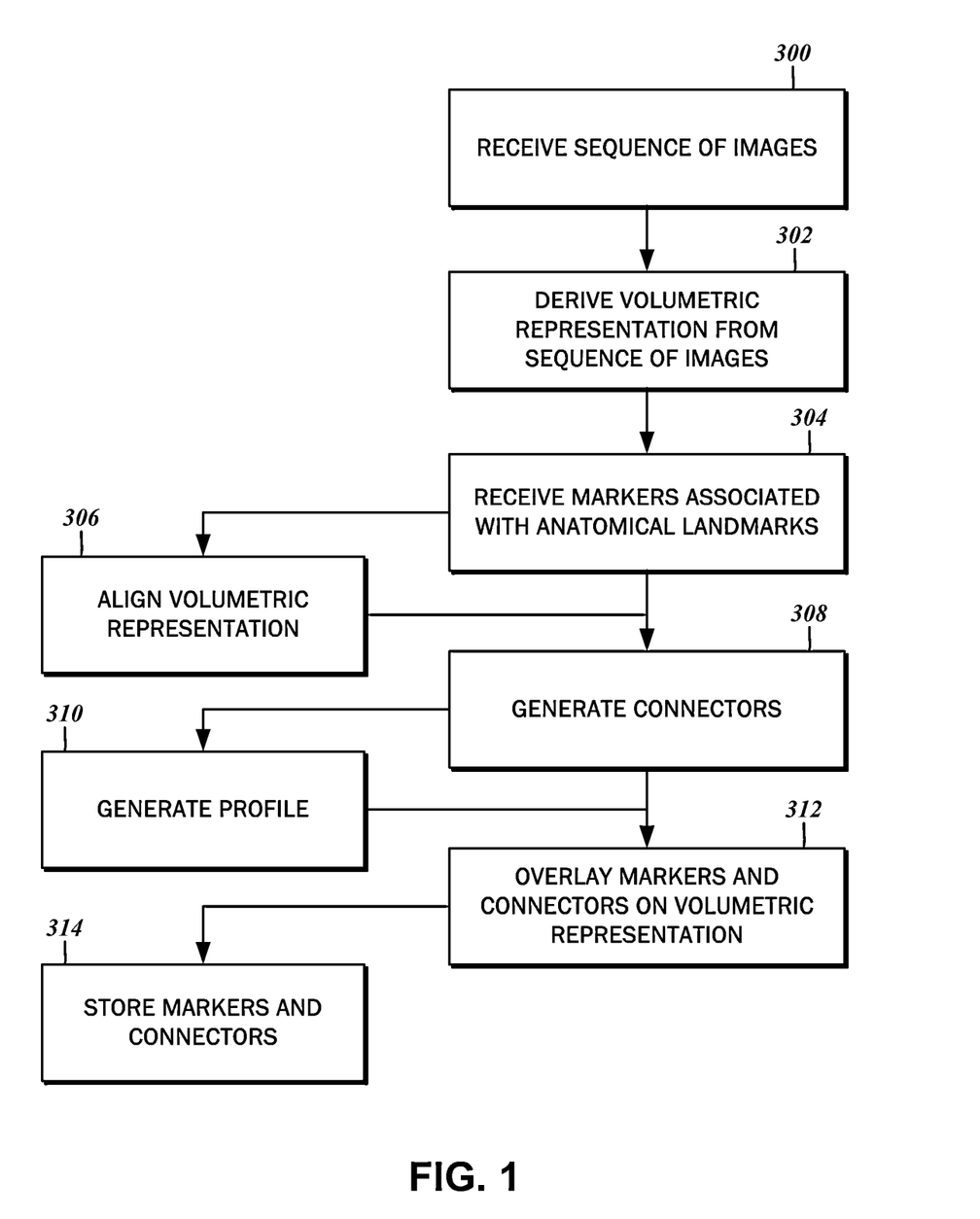
FIG. 1 is a flowchart illustrating one method for generating a cephalometric analysis of an orthodontic patient in accordance with one embodiment of the present disclosure.

Referring again to the flowchart of FIG. 1, the method for generating a cephalometric analysis continues with a step 304 of receiving one or more markers associated with particular anatomical landmarks of the patient's head 5. As is known in the art, the specific landmarks that are to be identified by the practitioner depend on the selected analysis method and the gender of the patient. In accordance with one embodiment, the practitioner can select from the Ricketts/Caucasian analysis, the Ricketts/Asian analysis, the Ricketts/African analysis, the Steiner analysis, and the Tweed analysis via an analysis selection control 44 on the toolbar 24. The analysis rules can be stored in an eXtended Markup Language (XML) document that may be modified by the practitioner and entirely new analysis rules can also be developed and stored independently. The gender of the patient is selected via a gender selection control 46, also selectable from the toolbar 24.

Upon selecting the analysis method and patient gender, the landmark selection pane 22 is populated with the various anatomical landmarks that the practitioner directly identifies on the images. By way of example only and not of limitation, for a Ricketts/Caucasian analysis method, the landmark selection pane 22 lists the following anatomical landmarks: Porion right/left, Condylion right/left, DC right/left, Gonion right/left, Xi right/left, Lower Bicuspid Crown right/left, Orbitale right/left, Pt right/left, Basion, Nasion, ANS, PNS, Point A, Point B, Pm, Pogonion, Gnathion, Menton, Upper Incisor Crown/Apex, Lower Incisor Crown/Apex, Upper Right Molar Mesial/Distal/Root Lingua, Lower Right Molar Mesial/Distal/Root Lingua, Upper Left Molar Mesial/Distal/Root Lingua, and Lower left Molar Mesial/Distal/Root Lingua.

A marker to be placed for the particular anatomical landmark is first highlighted on the landmark selection pane 22, and the corresponding location on the image is identified. A further input places the marker on the representation of the patient's head 5, and associates a set of coordinate values thereto. The practitioner sequentially places each of the markers as listed in the landmark selection pane 22. The markers can thus be visually located via the graphical user interface 10, specifically, the two-dimensional representations of the patient's head 5 generated on the first viewing pane 14, the second viewing pane 16, and the third viewing pane 18.

As the anatomical landmarks are placed, the volumetric representation is oriented correctly per step 306. More particularly, four landmarks are used to reset the position of the patient's head 5 in a virtual space, or along a first coordinate system. According to one embodiment, these landmarks are Porion right, Porion left, Orbitale right, and Orbitale left. This is understood to minimize patient positioning error and viewpoint magnification error, such that comparisons between successive imaging procedures are more easily made. Also in pane 20 the lines appear as the corresponding landmarks are chosen. Also, it is possible to move the landmarks once they are placed to fine-tune them. So rather than putting down a new landmark, if the cursor is near an existing one, it moves that one.

Upon completion, the method continues with a step 308 of generating connectors between one or more selected ones of the markers. This functionality may be invoked by pressing a tracing button 48 accessible from the toolbar 24. The connectors and the selection of particular anatomical landmarks are understood to be specific to the predefined analysis method. The lengths of the connectors, as well as the angular relationships between different connectors, are calculated. In further detail, the method may include calculating an actual length of one of the connectors, as well as an actual angular value between a selected pair of connectors. Since these variables can be consistently measured, standardized values based upon past research are known in the art, so the degree of deviations from the norm can be quantified.

Figure 3:
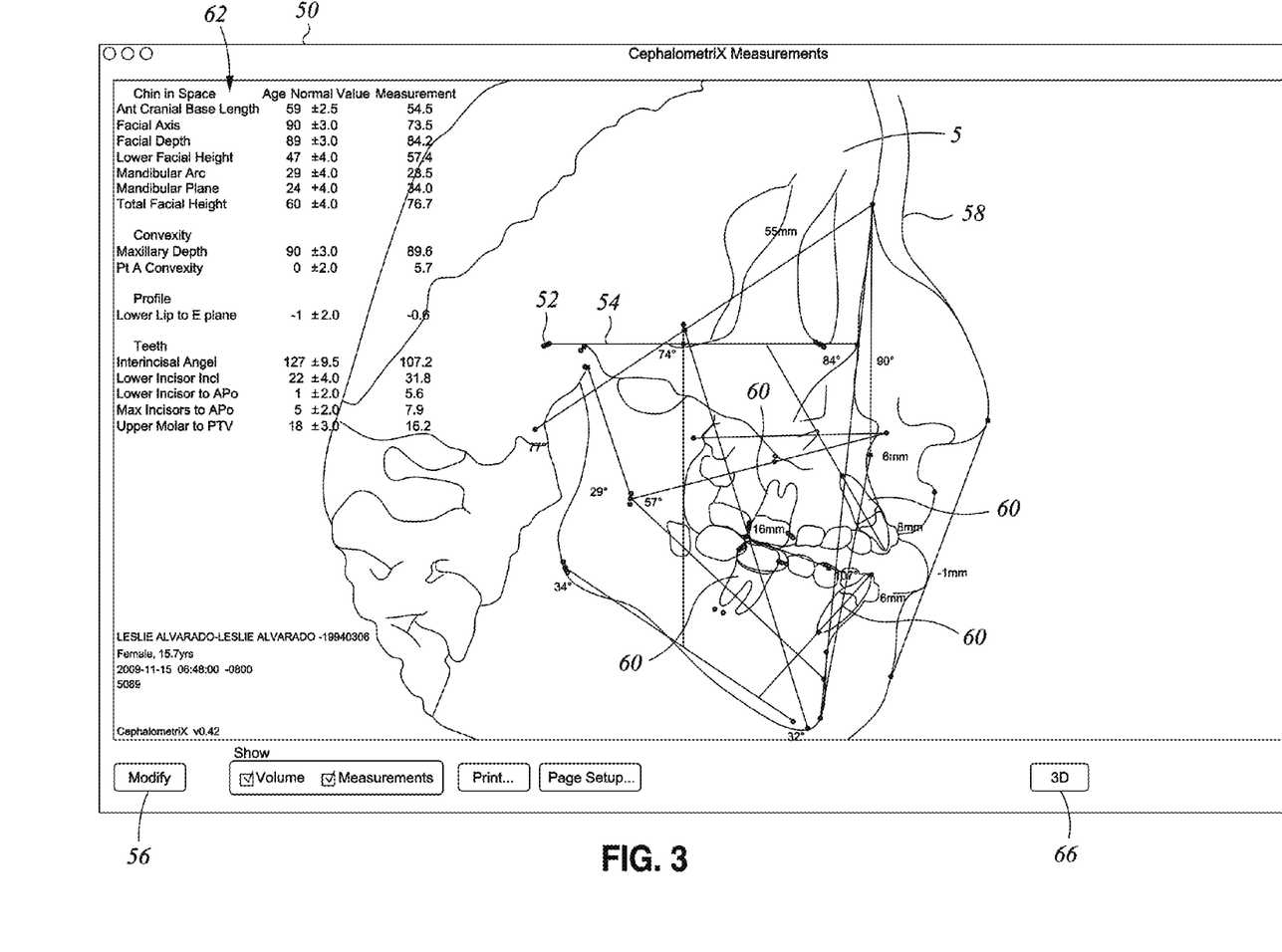
FIG. 3 is an exemplary two-dimensional measurement user interface of the plug-in module invoked after the patient's anatomical landmarks have been identified.

With reference to FIG. 3, as an intermediate step, the markers, connectors and the various measurements thereof may be displayed on a two dimensional measurements window 50. As shown, the different markers 52 are represented as dots, and are understood to correspond to anatomical landmarks. The connectors 54 are represented as lines between two different markers 52. Angular relationships between select connectors of interest are overlaid on the image, in addition to the length of certain connectors. From the measurements window 50, further modifications to the placement of the markers 5 may be performed by pressing the modify button 56 to return to the placement window 12.

The method of the present disclosure also contemplates a step 310 of generating a profile outline 58 of the patient based upon the received markers 52 and the generated connectors 54. As an initial step, the nose and chin points on the profile are located. Locating the noise point involves choosing the farthest point forward above point A. The chin point is located by moving forward from the Pogonion point until a soft tissue edge is detected. A point above and below the nose point is selected, and a circle is fitted to those three points. Additionally, a point above and below the chin point is selected, and a circle is similarly fitted to those three points. The radius of the fitted circles and the distance between the two circles is used to derive the common tangent between the two. The intersections of the common tangent and the circles are understood to be the nose and chin points. Adjustment to the profile outline may also be manually entered.

In accordance with one embodiment, the method includes overlaying a visual representation of one or more tooth templates. The tooth templates 60 are placed in the location of the first molars and incisors, and the side that is the furthest from ideal is shown. The tooth templates 60 are scaled to the same size as the patient's right molar, and placed in the proper orientation to match.

As indicated above, the actual length of the connectors and actual angles between different connectors can be measured and compared against a standardized norm. These relationships can be more generally characterized as quantified structural features, such as lower facial height, maxillary depth, and so forth. These characterizations, along with the respective norm values, variability, and actual measurements, may be displayed as an informational overlay 62.

Figure 4:
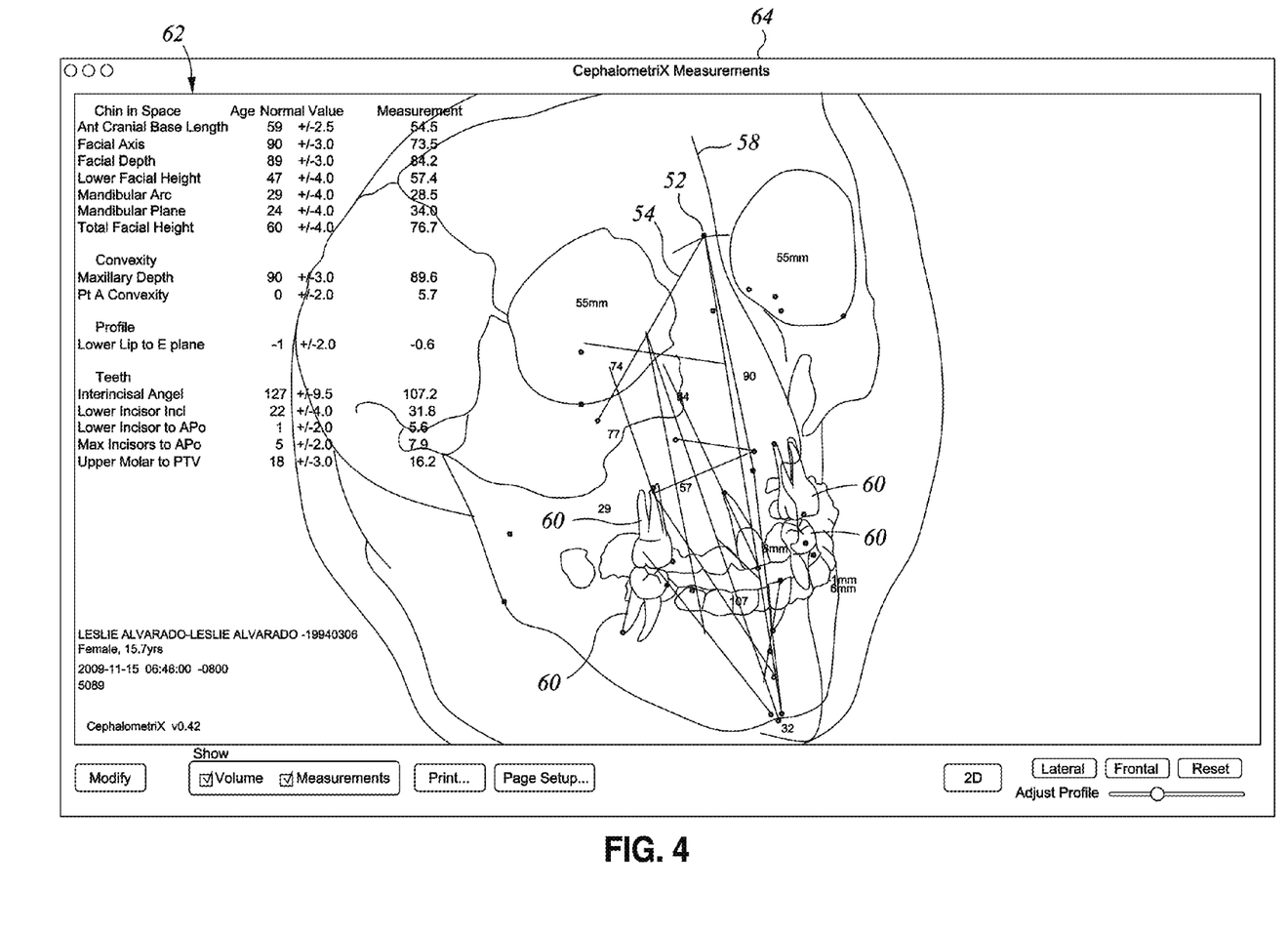
FIG. 4 is an exemplary three-dimensional measurement user interface of the plug-in module.

The graphics displayed on the two-dimensional measurements window 50 is understood to be static, but as shown in FIG. 4, an interactive three-dimensional measurements window 64 may output a volumetric representation of the patient's head 5. This functionality may be invoked from a 3D button 66 on the two-dimensional measurements window 50. In accordance with step 312, the method may include overlaying a visual representation of the markers 52, the connectors 54, and the profile outline 58 on the volumetric representation of the patient's head 5, along with the other information such as the angular relationships between select connectors of interest and the length of certain connectors in the same manner as discussed above in relation to the two dimensional measurements window 50 shown in FIG. 3. Further, the tooth templates may be similarly overlaid on the volumetric representation of the patient's head 5. Along these lines, the same information shown in the informational overlay 62 of the measurements window 50 may also be shown in the interactive three-dimensional measurements window 64. It is possible to rotate and otherwise manipulate the view of the volumetric representation in accordance with known three-dimensional graphics display/interaction techniques.

Not only is the volumetric representation valuable to the practitioner in diagnosing and treating malocclusions, it is also valuable in communicating treatment plans, goals, and procedures to the patient. In accordance with one embodiment, the computer executing the application may be connected to an interactive input/output device. The device may be receptive to simultaneous manual inputs, known in the art as gestures, to invoke different image navigation functions such as zooming, rotating, and moving about the display area. Furthermore, various levels of detail and layers of the patient's anatomical structures, including soft tissue, teeth, and hard tissue may be selectively displayed. Opacity levels and color for each layer may also be defined via a transfer function that can be similarly changed via multi-touch gestures. For purposes of convenience, these settings may be stored as presets that are readily accessible.

The volumetric representation can be further enhanced for patient visualization by projecting a photograph thereon. Corresponding points on the photograph and the volumetric representation can be selected, and the photograph can then be warped on to the volumetric representation. An alternative technique, however, involves capturing an image of the patient with a visibly overlaid checkerboard pattern and does not require the practitioner to manually locate corresponding points. Generally, the virtual scene of the volumetric representation is matched to the actual scene of the photograph. Therefore, the position of the camera, as well as the position and orientation of the patient in the x, y, z axes (6 degrees of freedom) is determined. Given a standardized size of the checkerboard, the position and orientation of the camera relative to such checkerboard can be ascertained. In conjunction with face-finding algorithms, the face of the patient as included in the photograph is segregated. The position of the camera as in the actual scene of the photograph is replicated in the virtual scene, such that the volumetric representation is positioned identically as the patient in the photograph. The photograph is then projected on to the volumetric representation. The coordinate system of the photograph is correlated to the coordinate system of the volumetric representation so that the two are properly aligned. In another embodiment, the face finding algorithm locates the face from both the volumetric representation as well as the photograph, and aligning the two with each other.

Another visual enhancement to the volumetric representation is the identification of tooth landmarks. The practitioner first identifies the occlusal plane, and the volumetric representation is re-sliced along that plane. In an axial view, each medial and distal tooth point is marked in the upper and lower teeth. The identification of these points is followed by generating a two-dimensional MIP view shown with the identified landmarks. It is contemplated that the points are adjustable inferiorly and superiorly.

Based upon two-dimensional growth standards from the frontal and saggital views, accurate three-dimensional models can be generated. In various embodiments, an overall best fit, or a best fit among specific anatomical landmarks, can be used to superimpose an age- and gender-matched standard over the volumetric representation of the patient's head 5, with the differences being shown in various colors or shades along a spectrum. For example, if the top jaw of the patient is positioned improperly with respect to the standard, then it can be colored red. The standards models can be fitted without scaling so that form differences can be ascertained, or with scaling to eliminate size differences so that shape differences can be ascertained.

Referring to the flowchart of FIG. 1, the method may also include storing the markers into an external data file per step 314. In this context, markers are understood to refer to the anatomical landmarks and the correspondingly identified coordinate values. Other data may also be included, however. The external data file may be an XML document so as to streamline data sharing with other applications capable of extracting data therefrom. It is contemplated that the obtained data may be used in research projects, developing more accurate average values, and so forth. According to one embodiment of the present disclosure, the step 304 of receiving the markers may actually originate from such an XML file. By way of example, the plugin module finds and opens a data file containing the markers, the procedure of manually locating the landmarks via the placement window 12 is skipped, and the method proceeds directly to step 312 relating to the display of the two-dimensional representation of the patient's head 5 and accompanying overlays on the two-dimensional measurements window 50, or to the display of the volumetric representation and accompanying overlays on the interactive three-dimensional measurements window 64.

Figure 5:
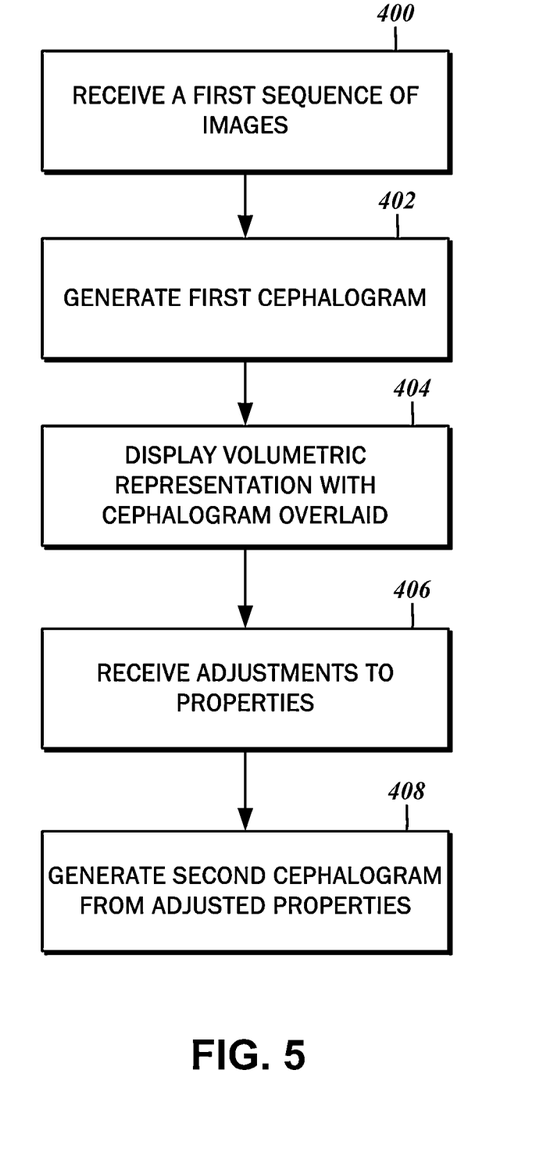
FIG. 5 is a flowchart illustrating a method for developing an orthodontic treatment plan in accordance with another embodiment of the present disclosure.

As noted above, the present disclosure also contemplates a method for developing an orthodontic treatment plan in which the practitioner determines the specific mechanics necessary for treating a patient. Referring to the flowchart of FIG. 5, the method begins with a step 400 of receiving a first sequence of images of the patient's head 5. It is understood that this step corresponds to step 300 discussed above, and by way of example, these images may be of the patient before initiating treatment. Thereafter, the method may continue with a step 402 of generating a first cephalogram from the first sequence of images and a plurality of landmarks of orthodontic structures identified on the images. Also as discussed above, the first cephalogram is understood to illustrate various relationships between the anatomical landmarks in accordance with the selected analysis method. These relationships are also referred to as properties of the cephalogram or the patient's head 5.

Figure 6:
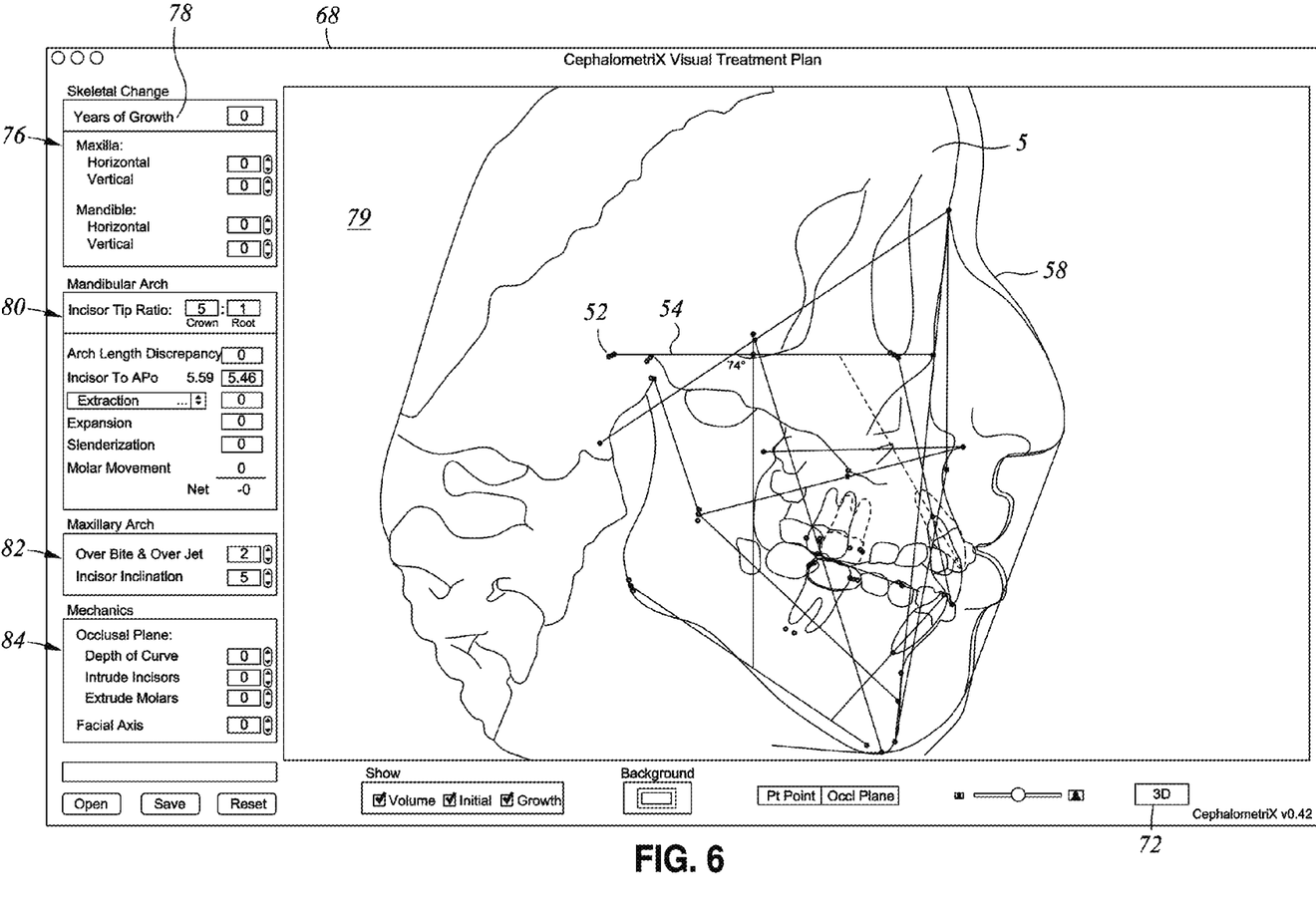
FIG. 6 is an exemplary two-dimensional treatment plan user interface.

FIG. 6 shows an exemplary two-dimensional treatment planning window 68 that includes a saggital MIP view of the patient's head 5 in a main display pane 69. In accordance with an embodiment shown in FIG. 7, a three-dimensional treatment plan window 70 is also contemplated. This view includes the volumetric representation of the patient's head 5 shown in a main display pane 71 per step 404 of the method for developing the orthodontic treatment plan, instead of the static two-dimensional MIP view shown in FIG. 6. It is possible to switch between these views by pressing the 3D button 72 on the two-dimensional treatment plan window 68, and the 2D button 74 on the three-dimensional treatment plan window 70. The various adjustments that can be made to the connectors 54 apply equally to the two-dimensional view and the three-dimensional view, so the following details are understood to apply to both.

Figure 7:
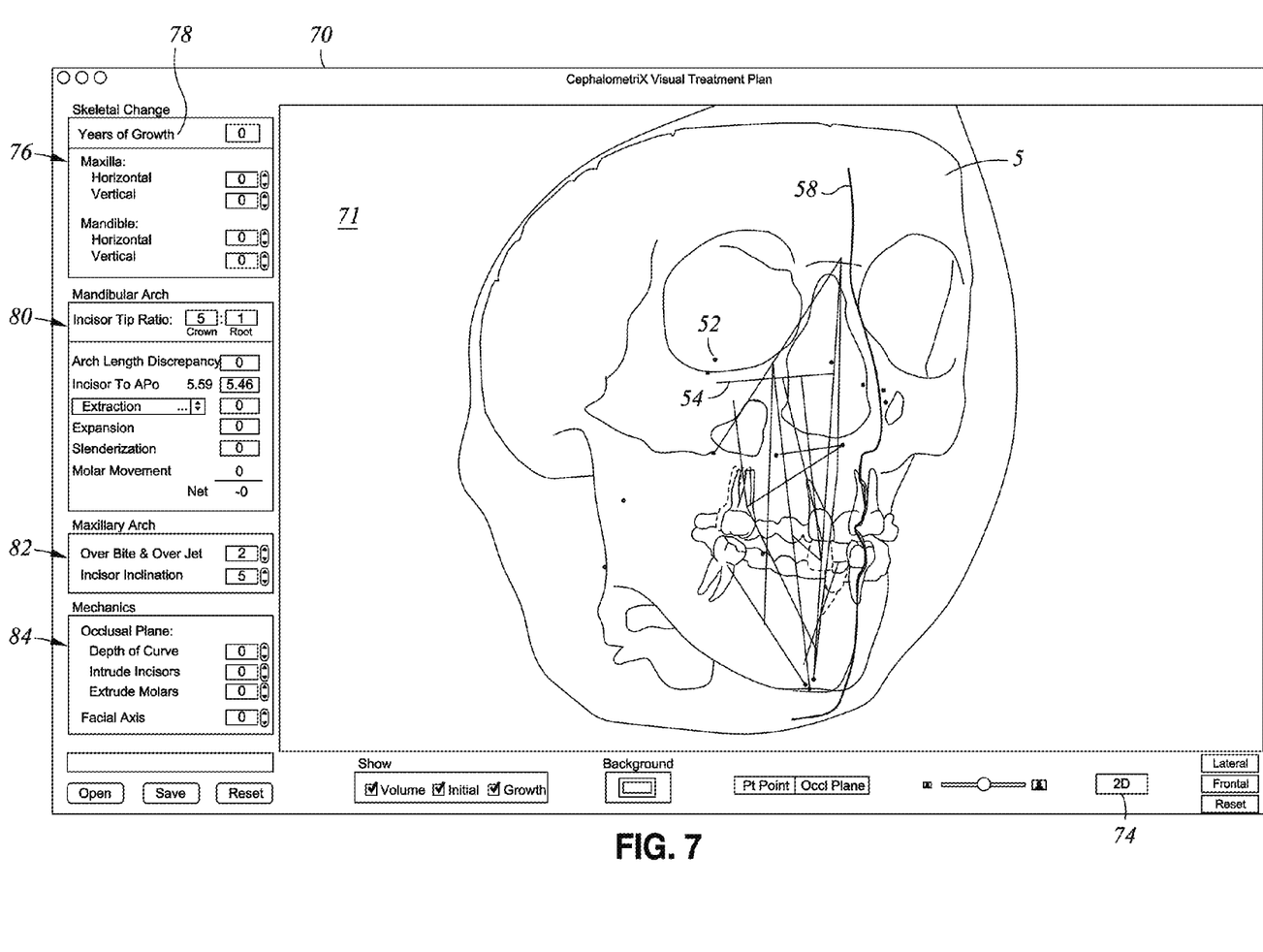
FIG. 7 is an exemplary three-dimensional treatment plan user interface.
Figure 8:
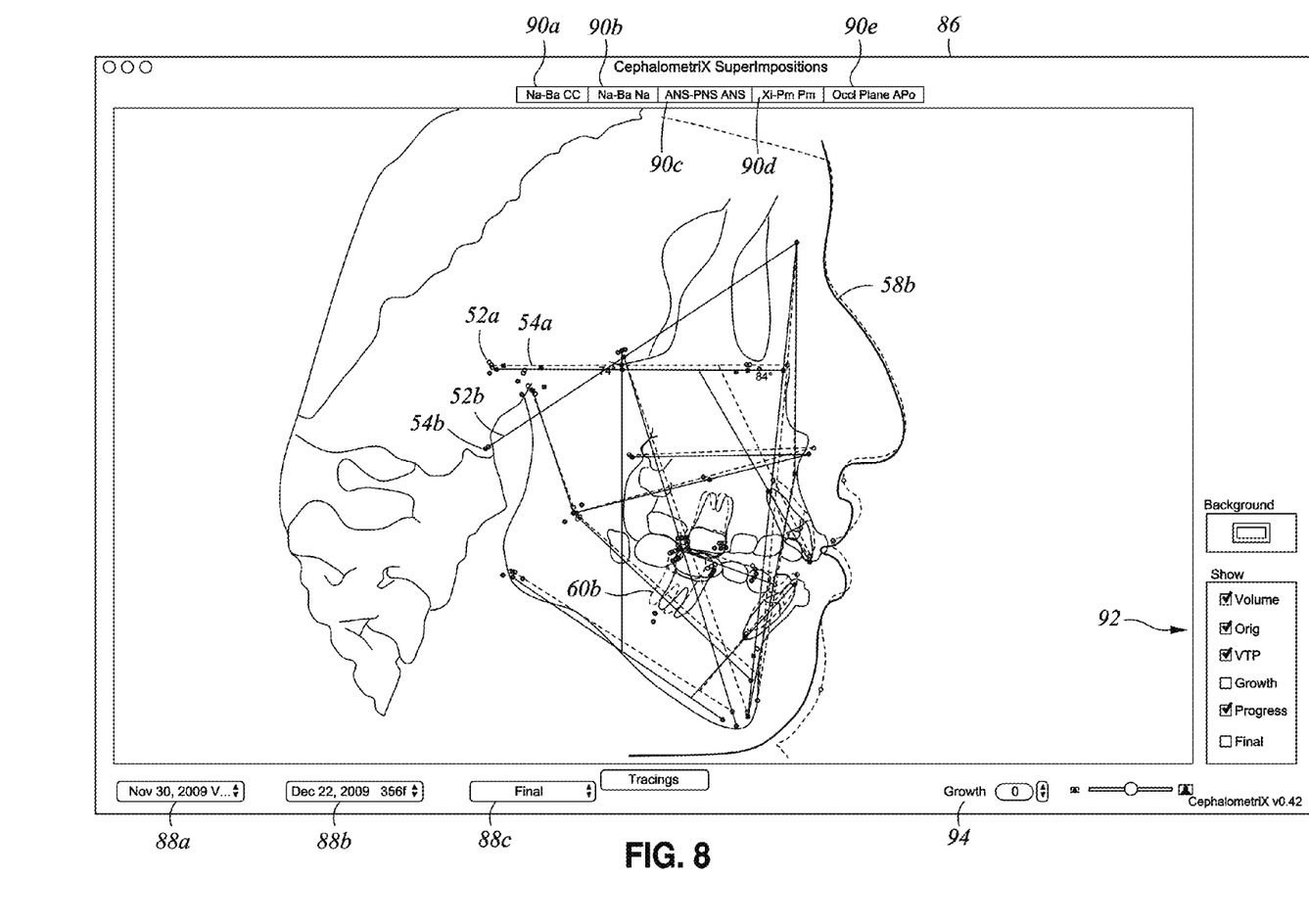
FIG. 8 is a superimposition user interface for comparing different cephalograms generated at different times.

With reference to the flowchart of FIG. 6, the method of developing the orthodontic treatment plan further includes a step 406 of receiving adjustments to one or more of the properties. As shown in FIGS. 7 and 8, the treatment plan windows 68, 70 include a property editing pane 76. More particularly, the property editing pane 76 is broken down into different sub-segments including a skeletal change panel 78, a mandibular arch panel 80, a maxillary arch panel 82, and a mechanics panel 84. Each of the sub-segments includes a listing of the properties that can be adjusted, along with numerical adjustment controls. In accordance with customary practice, treatment plans are developed with an assumption that the molars will finish in Class I, and the incisors will have proper over bite and over jet. In greater detail, the upper molars and the lower molars are set to Class I, the lower incisors are set 1 mm to the occlusal plane, and the upper incisors are set such that the crown tip is 2 mm in over bite and over jet with an angulation of +5 degrees to the facial axis.

As will be recognized by those having ordinary skill in the art, orthodontic treatment planning typically begins with skeletal changes, which sets the foundation for the treatment. Accordingly, it is one of the first adjustments that are made. Growth prediction may be incorporated, and involves the manipulation of how the upper and lower jaws relate to each other and to the cranial base. Adjustments to these properties are made via the skeletal change panel 78. If the practitioner attempts to adjust the growth of the patient beyond an average remaining growth period, a dialog box appears warning the practitioner there are a limited number of years left. For males, the limitation is 19.5 years, and for females, the limitation is 14.5 years. For example, if a male patient is 19 years old and the practitioner tries to grow him 2 years, the warning box will indicate that there is only 0.5 years of growth left, and change the entered value to that number.

The next step in treatment planning accounts for crowding in the lower jaw and the positioning of the teeth in the patient's face, properties otherwise generally referred to as the mandibular arch. Arch length discrepancy (ALD) is determined and entered, and the degree of movement necessary for the lower incisors to compensate for the crowding is determined. The practitioner identifies the desired final location of the incisors, and based upon the recalculated ALD, corrections to crowding by selecting one of extraction, expansion, and slenderizing (and the degree necessary for each such procedure) are entered. Where extraction is chosen, the average size of the tooth being extracted is accounted for. If the upper teeth are extracted by the lower teeth are not, the upper molars are set into Class II. On the other hand, if the lower premolar teeth are extracted but not the upper teeth, the upper molars are set into Class III. Extracting a lower incisor keeps the molars in class I. Slenderizing and expansion operations are likewise accounted for. The adjustments to these properties may be entered via the appropriately referenced mandibular arch change panel 80.

By default, the maxillary arch is set to 2 mm over bite and 2 mm over jet. However, it is possible for the practitioner to adjust these properties as well, along with the angulation of the upper incisor to change the rotating point around the crown point. Adjustments to these properties may be entered via the maxillary arch change panel 82.

In the mechanics change panel 84, the practitioner has the option of manipulating the occlusal plane in several ways, including depth of curve, intrude incisors, and extrude molars. It is understood that intruding the incisors rotates the occlusal plane around the Xi point, which effectively moves the anterior teeth up or down. Excluding the molars rotates the occlusal plane around Stomion, which effectively moves the posterior teeth up or down. Modifying the facial axis adjusts the way in which the patient's jaws open and close.

As discussed in greater detail above, the foregoing adjustable properties of the patient's anatomical structures are related to the specific positioning of the markers, and the length and angular relationships between the connectors 54 spanning different markers 52. Accordingly, adjustments to the properties are visually reflected in the two-dimensional and three-dimensional treatment planning windows 68, 70 as movement of the markers 52 and connectors 54. In accordance with one embodiment, a second cephalogram is generated per step 408 and also overlaid on the volumetric representation so that the practitioner can make a visual comparison as to the effects of the adjustment. Whenever subsequent changes are entered into the properties editing pane 76, it is understood that the visualization of the second cephalogram are updated in the main display panes 69, 71. These second cephalogram, also referred to as the visual treatment plan (VTP), is stored in a universally accessible XML file. Each patient case can also have numerous plans associated therewith.

Instead of interactively changing the second cephalogram overlaid on the volumetric representation, another embodiment contemplates superimposing a progress scan with a different sequence of images taken of the same patient at a different time. FIG. 8 shows a superimposition window 86 with the first set of markers 52a and connectors 54a corresponding to the first cephalogram, and a second set of markers 52b and connectors 54b corresponding to the second cephalogram. Updated tooth templates 60b, as well as an updated profile outline 58b are also overlaid on the volumetric representation. The second cephalogram is understood to be generated in the same manner as described above, that is, based upon a plot of the different anatomical landmarks according to a selected analysis method. The tracings/connectors cane be overlaid in the typical Ricketts superimposition areas, including Na—Ba at CC (designated by a selector 90a), Na—Ba at Na (designated by a selector 90b), ANS-PNS at NAS (designated by a selector 90c), Xi-Pm at Pm (designated by a selector 90d), and Occlusal Plane at Apo (designated by a selector 90e).

Figure 9A:
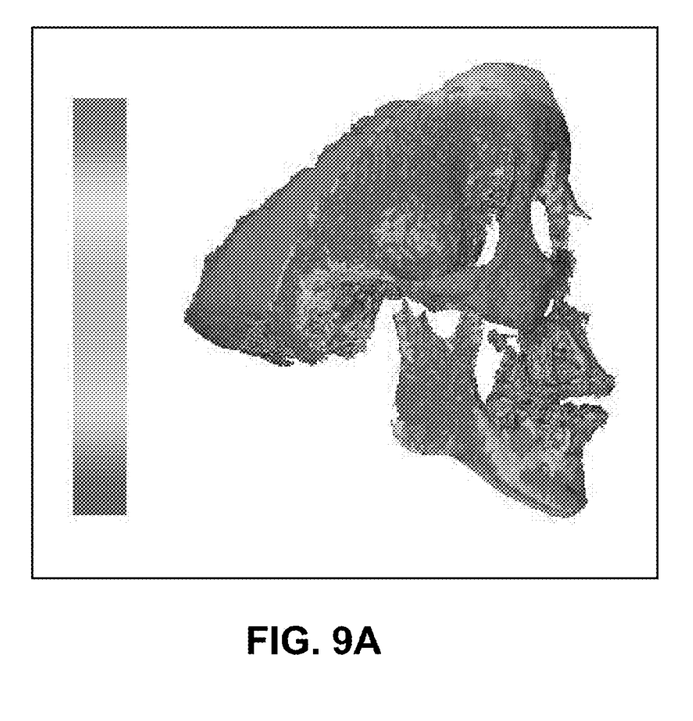
FIGS. 9A and 9B are exemplary visualizations of three-dimensionally superimposed growth standards.
Figure 9B:
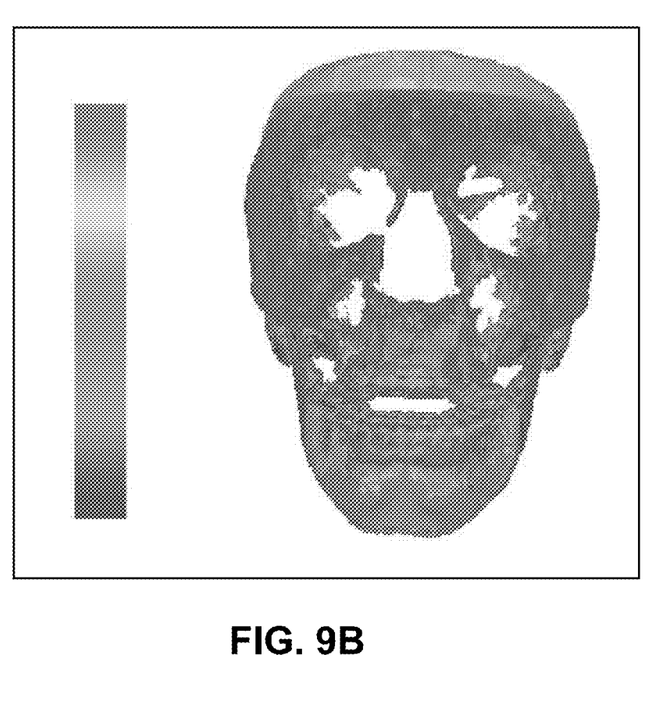

In one embodiment, three separate cephalograms may be concurrently displayed, as selected in cephalogram display controls 88a-c. Different features can be selectively displayed by checking and unchecking input boxes 92. In the particular example illustrated, the initial cephalogram, a progress cephalogram, and an anticipated completion cephalogram are selected and displayed in the superimposition window 86. As discussed above, skeletal growth may be accounted for by adjustments entered into a growth control 94. An example is shown in FIGS. 9A and 9B, where the volumetric representation associated with one cephalogram is superimposed on another volumetric representation associated with another cephalogram. The differences being color-coded in the same manner discussed above in relation to the three-dimensionally superimposed growth standards.

The particulars shown herein are by way of example only for purposes of illustrative discussion, and are presented in the cause of providing what is believed to be the most useful and readily understood description of the principles and conceptual aspects of the various embodiments set forth in the present disclosure. In this regard, no attempt is made to show any more detail than is necessary for a fundamental understanding of the different features of the various embodiments, the description taken with the drawings making apparent to those skilled in the art how these may be implemented in practice.

What is claimed is:

1. A method for generating a cephalometric analysis of an orthodontic patient, comprising:
   receiving a sequence of images each corresponding to a specific anatomical plane of the orthodontic patient;
   deriving a volumetric representation of the orthodontic patient from a combination of the sequence of the images;
   receiving one or more markers associated with particular anatomical landmarks of the orthodontic patient according to a predefined analysis method, the markers being defined by a set of coordinate values referenced to the volumetric representation and designated via an interactive user interface to a series of two-dimensional representations of axial views, coronal views, and saggital views corresponding to the received sequence of images, the markers being designated in at least each one of views;
   generating connectors between one or more selected ones of the markers in accordance with the predefined analysis method; and
   overlaying a visual representation of the markers and the connectors on the volumetric representation;
   generating a profile outline of the orthodontic patient without user intervention based upon a chin point and a nose point derived from the received markers; and
   overlaying a visual representation of the profile outline on the volumetric representation;
   wherein the chin point and the nose point are identified from an intersection of common tangents of a first fitted circle based around a farthest point forward above a received marker corresponding to a point A, and a second fitted circle based around a farthest point forward from a Pogonion point intersecting with a soft tissue edge.

2. The method of claim 1, wherein the interactive user interface includes a volumetric maximum intensity projection view.

3. The method of claim 1, further comprising:
   aligning the volumetric representation along a first coordinate system based upon one or more of the anatomical landmarks.

4. The method of claim 3, wherein the anatomical landmarks include porion right, porion left, orbitale right, and orbitale left.

5. The method of claim 1, further comprising:
   calculating an actual angular value between a selected pair of connectors; and
   displaying a predetermined normal angular value between the selected pair of connectors and the actual angular value between the selected pair of connectors.

6. The method of claim 1, further comprising:
   calculating an actual length of one of the connectors; and
   displaying a predetermined normal length of the one of the connectors and the actual length of one of the connectors.

7. The method of claim 1, further comprising:
   generating a profile outline of the orthodontic patient based upon the received markers and the generated connectors; and
   overlaying a visual representation of the profile outline on the volumetric representation.

8. The method of claim 1, further comprising:
   overlaying a visual representation of one or more predefined tooth templates on the volumetric representation, the positioning of the predefined tooth templates being based in part upon the anatomical landmarks.

9. The method of claim 8, wherein the tooth templates are scaled based on the size of a selected tooth.

10. The method of claim 1, further comprising:
    superimposing a growth standard on to the volumetric representation, deviations from the standard being highlighted along a visual spectrum corresponding to the degree of deviation.

11. The method of claim 1, further comprising:
    storing the markers into an external data file.

12. The method of claim 11, wherein the one or more markers are retrieved from the external data file.

13. The method of claim 1, further comprising:
    receiving a secondary image representative of a face of the patient; and
    projecting the secondary image onto the volumetric representation.

14. The method of claim 13, further comprising:
    receiving a first set of exterior landmarks on the volumetric representation; and
    receiving a second set of exterior landmarks on the secondary image;
    wherein the projecting of the secondary image onto the volumetric representation is based upon a matching of the first set of exterior landmarks to the respective corresponding second set of exterior landmarks.

15. The method of claim 1, wherein the sequence of images is generated by cone beam computed tomography.

16. An article of manufacture comprising a non-transitory program storage medium readable by a computer, the medium tangibly embodying one or more programs of instructions executable by the computer to perform a method for generating a cephalometric analysis of an orthodontic patient, comprising:
    receiving a sequence of images each corresponding to a specific anatomical plane of the orthodontic patient;

deriving a volumetric representation of the orthodontic patient from a combination of the sequence of the images;

receiving one or more markers associated with particular anatomical landmarks of the orthodontic patient according to a predefined analysis method, the markers being defined by a set of coordinate values referenced to the volumetric representation and designated via an interactive user interface to a series of two-dimensional representations of axial views, coronal views, and saggital views corresponding to the received sequence of images, the markers being designated in at least each one of views;

generating connectors between one or more selected ones of the markers in accordance with the predefined analysis method; and overlaying a visual representation of the markers and the connectors on the volumetric representation;

generating a profile outline of the orthodontic patient without user intervention based upon a chin point and a nose point derived from the received markers; and overlaying a visual representation of the profile outline on the volumetric representation;

wherein the chin point and the nose point are identified from an intersection of common tangents of a first fitted circle based around a farthest point forward above a received marker corresponding to a point A, and a second fitted circle based around a farthest point forward from a Pogonion point intersecting with a soft tissue edge.

* * * * *